United States Patent
Lynn et al.

(10) Patent No.: US 9,762,654 B2
(45) Date of Patent: Sep. 12, 2017

(54) SYSTEM AND METHOD FOR PROVIDING A USER INTERFACE TO REMOTELY CONTROL MEDICAL DEVICES

(71) Applicant: Abbott Medical Optics Inc., Santa Ana, CA (US)

(72) Inventors: Kyle E Lynn, Tustin, CA (US); Richard G Duff, Irvine, CA (US); Rennie G Allen, Lake Elsinore, CA (US); Michael J Claus, Newport Coast, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 381 days.

(21) Appl. No.: 13/833,547

(22) Filed: Mar. 15, 2013

(65) Prior Publication Data

US 2014/0280474 A1   Sep. 18, 2014

(51) Int. Cl.
G06F 15/16    (2006.01)
H04L 29/08    (2006.01)
G06F 19/00    (2011.01)

(52) U.S. Cl.
CPC .......... *H04L 67/10* (2013.01); *G06F 19/3418* (2013.01)

(58) Field of Classification Search
CPC ............................. G06F 19/3418; H04L 67/10
USPC .................................. 709/203, 204, 205, 206
See application file for complete search history.

(56) References Cited

U.S. PATENT DOCUMENTS

| | | | |
|---|---|---|---|
| 2007/0208833 A1* | 9/2007 | Bucholz | 709/220 |
| 2007/0244691 A1* | 10/2007 | Alwan et al. | 704/8 |
| 2008/0115146 A1 | 5/2008 | Claus et al. | |
| 2013/0006603 A1* | 1/2013 | Zavatone et al. | 704/2 |
| 2013/0176230 A1* | 7/2013 | Georgiev et al. | 345/173 |

FOREIGN PATENT DOCUMENTS

EP   1830521 A2   9/2007

OTHER PUBLICATIONS

International Search Report and Written Opinion for Application No. PCT/US2014/018557, mailed on Jul. 11, 2014, 10 pages.

\* cited by examiner

*Primary Examiner* — Normin Abedin
(74) *Attorney, Agent, or Firm* — Abbott Medical Optics Inc.

(57) ABSTRACT

Systems and methods for remotely controlling a medical device are disclosed. Such systems and methods may include the providing of computer executable instructions for presenting a graphical user interface capable of providing remote user input to the medical device, wherein the graphical user interface is at least substantially a true screen representation of an interface of the at least one medical device. At least one network port may be capable of remotely receiving the user input information. Responsive to the input information, a driver associated with the medical device may be configured to control the medical device responsive to the input at the remote graphical user interface.

12 Claims, 6 Drawing Sheets

SYSTEM AND METHOD FOR PROVIDING A USER INTERFACE TO REMOTELY CONTROL MEDICAL DEVICES

FIELD OF THE DISCLOSURE

The instant disclosure relates to the control of medical devices, and in particular, to systems and methods for providing a user interface to remotely control medical devices.

BACKGROUND OF THE DISCLOSURE

It goes without saying that the advances in medical and surgical technologies in the modern era are due, in large measure, to the advances made in the devices used during these surgical/medical procedures. However, these advanced devices require advanced expertise for operation, and this advanced expertise may not be available in all surgical environments. For example, surgical environments in remote locations may not have access to those environments doctors or nurses with expertise commensurate with that required to use and operate modern surgical equipment.

One proposed solution to a lack of local operational expertise for advanced medical equipment is the use of wireless remote surgical device control. However, present wireless remote surgical solutions are difficult to use, and provide inadequate surgical techniques for "on the fly" surgical modifications. Further, presently available remote solutions are limited as to the interoperability of various equipment types, and are not suited for use by operators speaking different languages.

Attempts to address these and other difficulties have not only been unsuccessful, but have further added complexity into surgical systems, and, more particularly, into the user interfaces for remotely-controllable surgical solutions. Moreover, even with the additional complexities of these remote user interfaces, current remote control systems are not complex enough to dynamically adapt to allow for dynamic interactions between highly complex user interfaces and surgical hardware systems. These complexities have also, thus far, precluded the development of a remote control surgical system that is context sensitive, such as for a non-sterile nurse or surgeon to use in order that such non-sterile party could perform all functions, or substantially all functions, that are typically performed by sterile parties local to the surgical environment.

More particularly, currently proposed solutions include the use of a wireless remote control unit that pairs to a surgical system via, for example, Bluetooth or infrared technology, and that enables some control over the surgical system without necessitating a scrub-in. However, such presently available remote control solutions typically provide a user interface having a fixed number of mechanical buttons that allow for navigation of the user interface display. These mechanical buttons generally provide fixed functionality and fixed physical labels. That is, the function and nomenclature of the buttons are limited and cannot be changed, regardless of what the user encounters on the user interface display and/or during a procedure or pre-procedure in the surgical environment remote from the user.

Therefore, the need exists for a remote surgical system and method that alleviates complexity in available remote surgical systems. This remote system and method may allow for the providing of a remote surgical interface on any device, and particularly on any mobile device, thereby providing a remote surgical system having interoperability with various types and manufacturers of surgical hardware, and allowing for interrelation between a remote party and a local surgical environment in any of a myriad of languages.

BRIEF DESCRIPTION OF THE FIGURES

Understanding of the present invention will be facilitated by consideration of the following detailed description of the preferred embodiments of the present invention taken in conjunction with the accompanying drawings, in which like numerals refer to like parts.

SUMMARY OF THE DISCLOSURE

Figure 1:
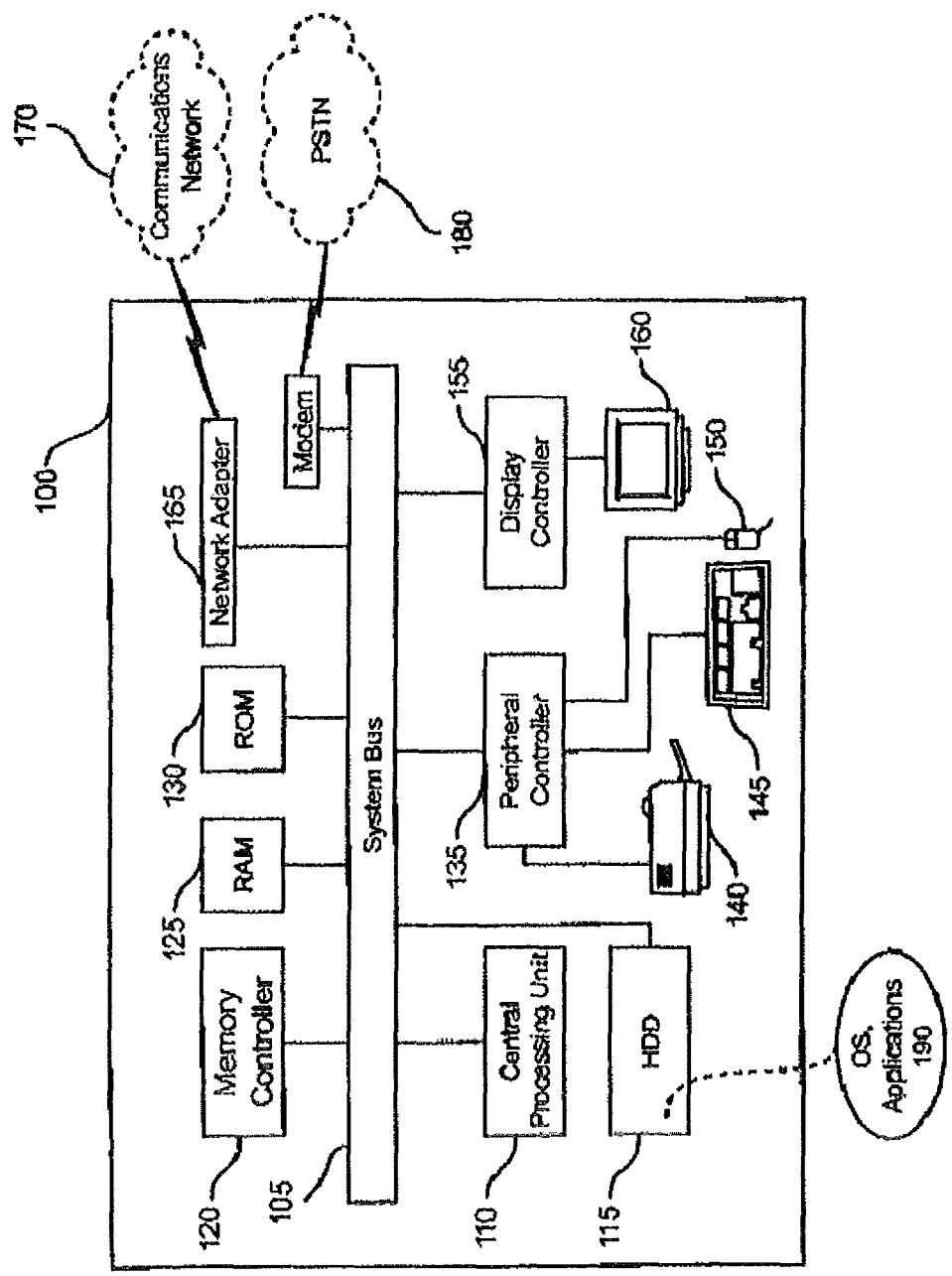
FIG. 1 illustrates a diagram of an exemplary computing system according to embodiments of the present invention.

The present disclosure provides systems and methods for providing a user interface to remotely control medical devices.

Systems and methods for remotely controlling a medical device are disclosed. Such systems and methods may include the providing of computer executable instructions for presenting a graphical user interface capable of providing remote user input to the medical device, wherein the graphical user interface is at least substantially a true screen representation of an interface of the at least one medical device. At least one network port may be capable of remotely receiving the user input information. Responsive to the input information, a driver associated with the medical device may be configured to control the medical device responsive to the input at the remote graphical user interface. The graphical user interface may comprise a screen that displays the same controls as that of a screen on the medical device.

Thus, the present disclosure provides a remote surgical system and method that alleviates complexity in available remote surgical systems. This remote system and method allows for the providing of a remote surgical interface on any device, and particularly on any mobile device, thereby providing a remote surgical system having interoperability with various types and manufacturers of surgical hardware, and allowing for interrelation between a remote party and a local surgical environment in any of a myriad of languages.

DETAILED DESCRIPTION OF THE EMBODIMENTS

It is to be understood that the figures and descriptions of the present disclosure have been simplified to illustrate elements that are relevant for a clear understanding of the present invention, while eliminating, for the purposes of clarity and brevity, many other elements found in typical network-communicative systems, mobile devices, servers and methods. Those of ordinary skill in the art may thus recognize that other elements and/or steps are desirable and/or required in implementing the present invention.

However, because such elements and steps are well known in the art, and because they do not facilitate a better understanding of the present invention, a discussion of such elements and steps is not provided herein. The disclosure herein is directed to all such variations and modifications to the disclosed elements and methods known to those skilled in the art.

The disclosure provides a remote, wireless surgical system and method that may employ a software application, or "app", that may be particularly useful on smart devices, such as cellular phones, tablet computers, and the like, to provide remote control of one or more aspects of a local medical/surgical environment. More particularly, the software app may provide a "true screen" to the remote user by the user interface, wherein the true screen is a substantial or precise re-creation of the screen or screens that are locally displayed on one or more surgical devices and/or systems in the surgical environment. This, of course, may allow for use/control of aspects of the local surgical environment by the remote user just as if the remote user was present in the surgical environment. Accordingly, the disclosure provides a remote control system that is context sensitive based on the local displays in the surgical environment. Moreover, the disclosure may allow a remote user to switch between displays for various devices in the local surgical environment, and in such instances the controls for the remote surgical system app may vary based on the hardware or software controls that are available in the surgical environment.

FIG. 1 depicts an exemplary computing system 100 for use in accordance with herein described system and methods. Computing system 100 is capable of executing software, such as an operating system (OS) and a variety of computing applications 190. The operation of exemplary computing system 100 is controlled primarily by computer readable instructions, such as instructions stored in a computer readable storage medium, such as hard disk drive (HDD) 115, optical disk (not shown) such as a CD or DVD, solid state drive (not shown) such as a USB "thumb drive," or the like. Such instructions may be executed within central processing unit (CPU) 110 to cause computing system 100 to perform operations. In many known computer servers, workstations, personal computers, and the like, CPU 110 is implemented in an integrated circuit called a processor.

It is appreciated that, although exemplary computing system 100 is shown to comprise a single CPU 110, such description is merely illustrative, as computing system 100 may comprise a plurality of CPUs 110. Additionally, computing system 100 may exploit the resources of remote CPUs (not shown), for example, through communications network 170 or some other data communications means.

In operation, CPU 110 fetches, decodes, and executes instructions from a computer readable storage medium such as HDD 115. Such instructions may be included in software such as an operating system (OS), executable programs such as the aforementioned "apps", and the like. Information, such as computer instructions and other computer readable data, is transferred between components of computing system 100 via the system's main data-transfer path. The main data-transfer path may use a system bus architecture 105, although other computer architectures (not shown) can be used, such as architectures using serializers and deserializers and crossbar switches to communicate data between devices over serial communication paths. System bus 105 may include data lines for sending data, address lines for sending addresses, and control lines for sending interrupts and for operating the system bus. Some busses provide bus arbitration that regulates access to the bus by extension cards, controllers, and CPU 110. Devices that attach to the busses and arbitrate access to the bus are called bus masters. Bus master support also allows multiprocessor configurations of the busses to be created by the addition of bus master adapters containing processors and support chips.

Memory devices coupled to system bus 105 may include random access memory (RAM) 125 and/or read only memory (ROM) 130. Such memories include circuitry that allows information to be stored and retrieved. ROMs 130 generally contain stored data that cannot be modified. Data stored in RAM 125 can be read or changed by CPU 110 or other hardware devices. Access to RAM 125 and/or ROM 130 may be controlled by memory controller 120. Memory controller 120 may provide an address translation function that translates virtual addresses into physical addresses as instructions are executed. Memory controller 120 may also provide a memory protection function that isolates processes within the system and isolates system processes from user processes. Thus, a program running in user mode may normally access only memory mapped by its own process virtual address space; in such instances, the program cannot access memory within another process' virtual address space unless memory sharing between the processes has been set up.

In addition, computing system 100 may contain peripheral controller 135 responsible for communicating instructions using a peripheral bus from CPU 110 to peripherals, such as printer 140, keyboard 145, and mouse 150. An example of a peripheral bus is the Peripheral Component Interconnect (PCI) bus.

Display 160, which is controlled by display controller 155, may be used to display visual output and/or presentation generated by or at the request of computing system 100, responsive to operation of the aforementioned computing program, such as an app. Such visual output may include text, graphics, animated graphics, and/or video, for example. Display 160 may be implemented with a CRT-based video display, an LCD or LED-based display, a gas plasma-based flat-panel display, a touch-panel display, or the like. Display controller 155 includes electronic components required to generate a video signal that is sent to display 160.

Further, computing system 100 may contain network adapter 165 which may be used to couple computing system 100 to external communication network 170, which may include or provide access to the Internet, an intranet, an extranet, or the like. Communications network 170 may provide user access for computing system 100 with means of communicating and transferring software and information electronically. Additionally, communications network 170 may provide for distributed processing, which involves several computers and the sharing of workloads or cooperative efforts in performing a task. It is appreciated that the network connections shown are exemplary and other means of establishing communications links between computing system 100 and remote users may be used.

Network adaptor 165 may communicate to and from network 170 using any available wired or wireless technologies. Such technologies may include, by way of non-limiting example, cellular, Wi-Fi, Bluetooth, infrared, or the like.

It is appreciated that exemplary computing system 100 is merely illustrative of a computing environment in which the herein described systems and methods may operate, and does not limit the implementation of the herein described systems and methods in computing environments having differing components and configurations. That is to say, the inventive concepts described herein may be implemented in various computing environments using various components and configurations.

Figure 2:
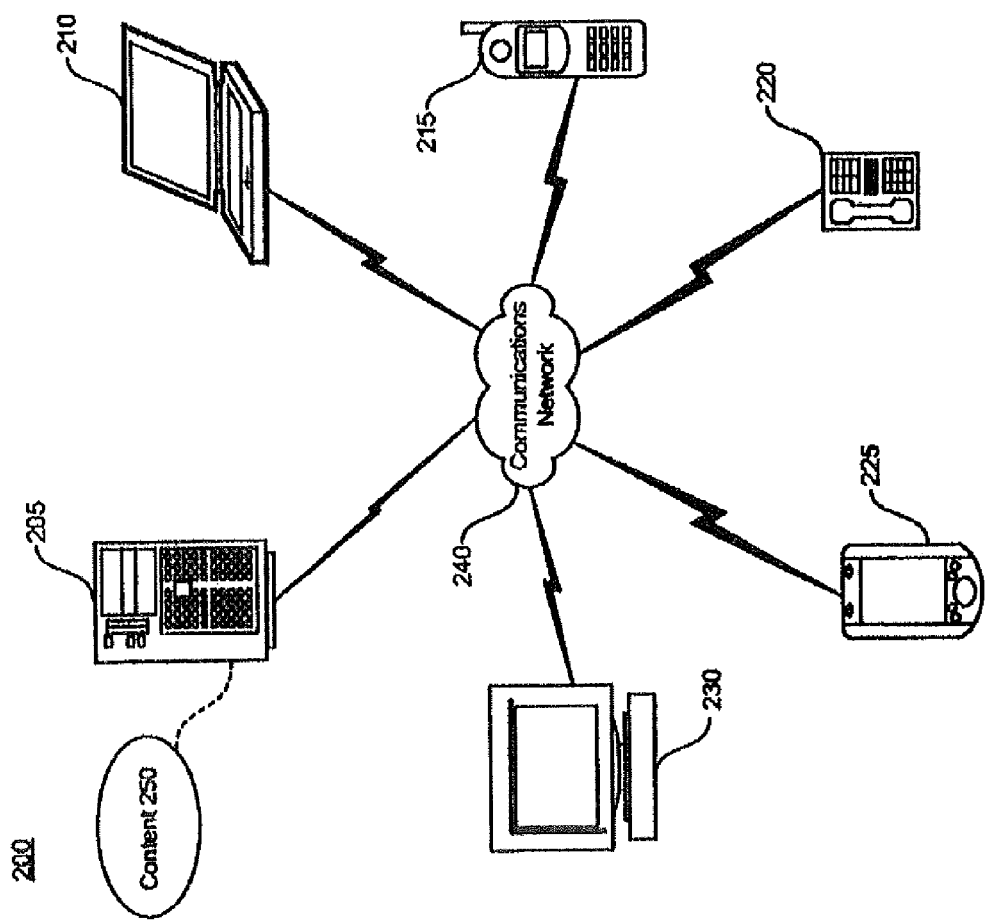
FIG. 2 illustrates a diagram of a system according to embodiments of the present invention.

As shown in FIG. 2, computing system 100 may be deployed in networked computing environment 200. In general, the above description for computing system 100 applies to server, client, and peer computers deployed in a networked environment, for example, server 205, laptop computer 210, and desktop computer 230. FIG. 2 illustrates an exemplary illustrative networked computing environment 200, with a server in communication with client computing and/or communicating devices via a communications network, in which the herein described apparatus and methods may be employed.

As shown in FIG. 2, server 205 may be interconnected via a communications network 240 (which may include any of, or any combination of, a fixed-wire or wireless LAN, WAN, intranet, extranet, peer-to-peer network, virtual private network, the Internet, or other communications network such as POTS, ISDN, VoIP, PSTN, etc.) with a number of client computing/communication devices such as laptop computer 210, wireless mobile telephone/smart device 215, wired telephone 220, personal digital assistant 225, user desktop computer 230, and/or other communication enabled devices (not shown). Server 205 may comprise dedicated servers operable to process and communicate data such as digital content 250 to and from client devices 210, 215, 220, 225, 230, etc. using any of a number of known protocols, such as hypertext transfer protocol (HTTP), file transfer protocol (FTP), simple object access protocol (SOAP), wireless application protocol (WAP), or the like. Additionally, networked computing environment 200 may utilize various data security protocols such as secured socket layer (SSL), pretty good privacy (PGP), virtual private network (VPN) security, or the like. Each client device 210, 215, 220, 225, 230, etc. may be equipped with an operating system operable to support one or more computing and/or communication applications, or "apps", such as a web browser (not shown), email (not shown), the dedicated user interfaces and medical device controls discussed herein, or the like, to interact with server 205.

Figure 3:
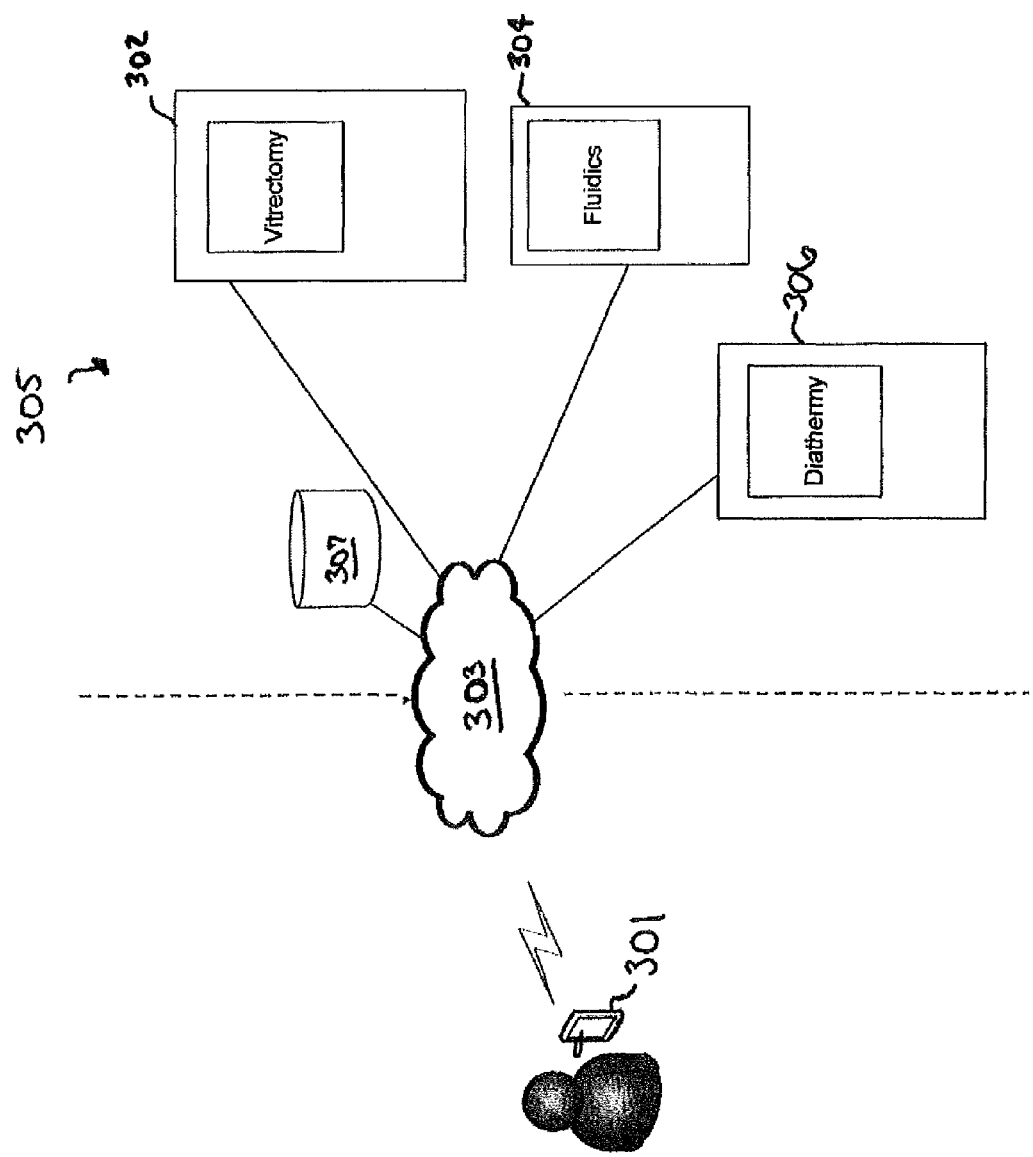
FIG. 3 illustrates a diagram of a system according to embodiments of the present invention.

In accordance with the disclosure, and with respect to FIG. 3, embodiments of the present invention may employ an app running on a client device 301 in a computing environment such as that discussed above with respects to FIGS. 1 and 2. The app may interface with electronic devices in various remote environments (for example, a surgical environment in which various surgical devices 302, 304, and 306 may be located) in substantially real time, such as through a central communication hub 303 (or a local communication hub) communicative with the local surgical environment(s) 305.

The one or more hubs 303 may be a server implemented on the Internet, in an implementation commonly referred to as "the cloud". Accordingly, the one or more hubs 303 may accumulate, or "log", data across a great many surgical procedures, and this data may be stored, for example, at a central storage location 307 associated with the central hub 303, such that any, many, or any authorized, remote user may access such logs. Thereby, the remote user interface may provide a data collection interface that may be used by local or remote surgeons and nurses.

Logged information, such as to any storage database, may include local surgical device settings and parameters, remote app interactions, surgical device parameters (and whether set locally or remotely), frequent actions taken using a surgical device, and the like, which may or may not be related to particular surgeons, patients, patient types, surgeon types, equipment types, surgical procedure types, and the like. Further, preferred surgical procedures, parameters, settings, and the like. The logged data may thus be saved, uploaded, or downloaded, such as for frequent and/or repeated use by a remote user. Moreover, the accumulation of information may allow for automated or manual/user requested recommendations during a procedure, such as wherein less frequently encountered anomalies arise during a surgical procedure, and wherein the availability of a large number of logs, which may be searchable by a remote user (such as based on a keyword or keywords indicative of the anomaly) may allow for a remote or local user to upload certain parameters that readily allow for the anomaly to be addressed.

Further, the logged information stemming from use of the app may include error logs, event logs, device failure logs, and the like, and accordingly the network connectivity and data log may allow for the capability of using the remote device to debug, upgrade, update, correct, and/or service a surgical device remote from the user and resident in the local surgical environment. Yet further, this allows for the storage, such as at the aforementioned central hub 303, of all pertinent information regarding local surgical devices and settings, errors, "bug" fixes, and the like, which may enable field service engineers to track serial numbers, device history records, and the like, such as for on-site service or remote customer support. That is, the remote app may "read" the serial numbers, or the like, of all equipment in a local surgical environment upon connecting the remote user to the local surgical environment. Thereby, equipment specifics, or "specs," once read by the remote app, may be ultimately stored at the central hub, and, as mentioned earlier, may be relationally stored in conjunction with numerous parameters, settings, errors, required updates, and the like. Thus, a service mode may be made available using the disclosed embodiments, wherein upgrades or other service features, such as for devices in a local surgical environment, may be "pushed" by a remote user, rather than needing to be "pulled" by a local surgical environment user, thereby further ensuring that surgical device software is maintained as updated.

Central tracking and logging capability may further allow, for example, for inventory tracking across one or many facilities. For example, each facility (or a plurality of co-owned or controlled facilities) may have secure access to the central hub, which, through the aforementioned data logging, provides information regarding supplies used during surgery, IOLs implanted during surgery, devices used during surgery, device failures during surgery, and the like. Thereby, each facility may have a de facto inventory of, for example, the need to refresh inventories of supplies, IOLs, upgrades or replacements to surgical devices, and the like. Moreover, each facility may set thresholds that, once surpassed, may automatically cause to be executed reorders of inventory items that number less than the threshold.

Figure 4:
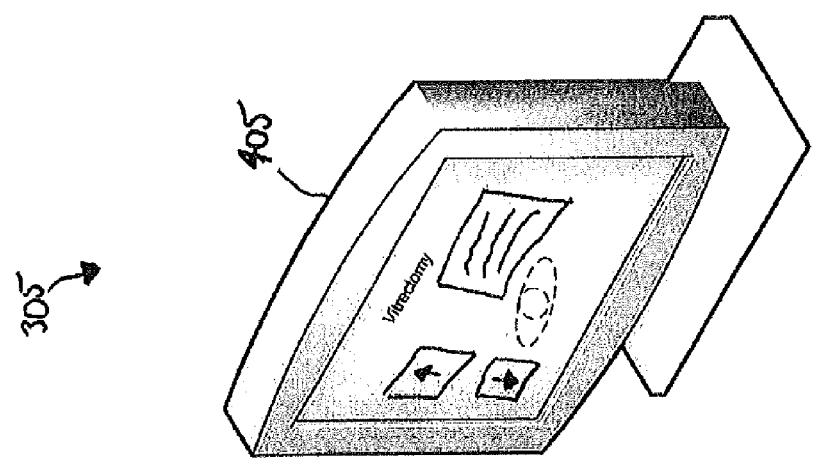
FIG. 4 illustrates an exemplary display screen according to embodiments of the present invention.
Figure 4:
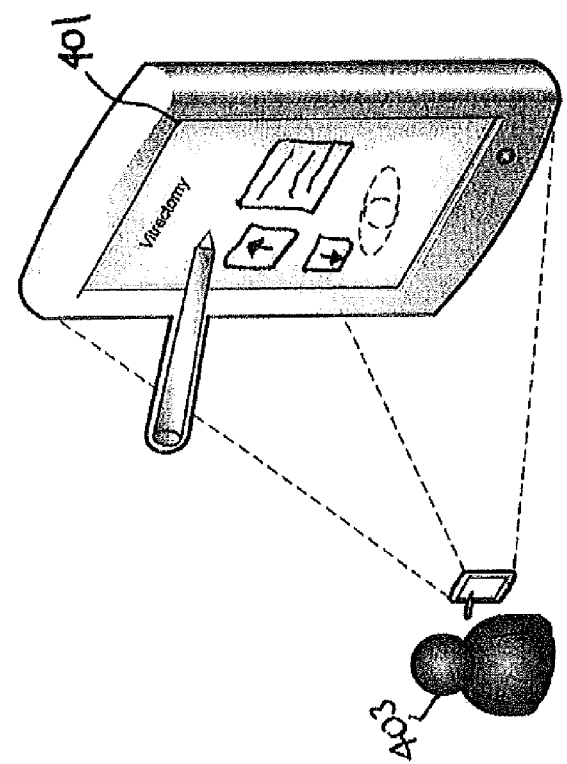

FIG. 4 is an exemplary display of a remote user interface 401 for controlling a device remotely connected to a surgical environment 305 according to embodiments of the disclosure. Specifically, FIG. 4 illustrates an example of a software app providing a "true screen" to the remote user 403 via the remote user interface 401, wherein the true screen is a substantial or precise re-creation of a screen that is viewable on a local display 405 of a medical device (e.g. a vitrectomy module 302) in the surgical environment 305. This true screen, of course, allows for remote use of the local surgical system by the remote user 403 just as if the remote user 403 was present in the local surgical environment.

The remote user interface may thus vary dynamically according to that which may be controlled in the surgical environment by the remote user. Further, the remote app may allow for the dynamic changing of any aspect of the user interface, such as in accordance with user preferences, i.e., if there are 3 available true screens for 3 different vitrectomy modules, the user may select a preferred true screen, even if not correspondent to the actual vitrectomy module in the local environment to be remotely controlled, and the app will "normalize" the user interface controls to allow the user to control an "A-type" vitrectomy module using a "B-type" vitrectomy module interface. Further, for example, the user language may thus be changed in accordance with the native language of the remote user, and the user interface language provided to the remote user may be different than the language employed by the users in the local surgical environment. That is, the system and method of the disclosure may display controls in a first language, which may occur in the local surgical environment in a language native for the surgeon or the scrub nurse, and the remote user interface may display in a second, different language native to the non-sterile surgeon or nurse. Yet further, the remote and local systems may provide a "chat" translation feature through the app interface to the local environment, wherein exchanges may occur between persons in the local surgical environment and the user of the remote user interface even in the event the local and remote users do not speak the same language.

Thereby, full user interface and control is granted to a remote user, just as if the remote user was in the surgical environment. Further, translation of instructions may occur as between the remote user and the local users in the surgical environment, and machine translations may occur as between the remote user-entered instructions and the machine language spoken by the hardware devices in a surgical environment. As such, a remote user may be enabled to select a preferred presentation of display and controls for a particular surgical aspect, regardless of the manufacturer or type of surgical device employed in the local environment, or the remote user may be enabled to see precisely the display and controls remotely that are presented in the local surgical environment.

In view of the above, the disclosure provides a multi-view machine, wherein the same or different views may be available locally or remotely. Moreover, multi-views, such as correspondent to different devices in the local surgical environment, may be provided by the graphical user interface of the present invention either simultaneously or alternately. That is, the presentation layer may allow for data correspondent to different devices (in the data layer) in the local surgical environment to be presented to the user at the same time, such as using a split screen, or may allow the user to alternate between presentation correspondent to the different devices, such as by "toggling" between views.

Further, the disclosure provides a translation and dictionary system, for both computer languages and spoken languages. In a particular embodiment, the data architecture of the present invention may be separate from the display architecture of the present invention. That is, the presentation layer of the present system and method may be maintained as separate from the data or action layers. Thereby, the translation of spoken languages, the interaction with devices of different device types and manufacturers, and the translation of log data from one machine type to another, may be performed in the data layer of the architecture of the disclosure. These may be maintained as distinct from the presentation layer, wherein the presentation layer may provide a uniform display locally and remotely based on machine type or preferred user, i.e., data, settings. As such, data may be normalized or directly translated in the data layer in the instant invention, and this data normalization may be performed locally, remotely, or in the cloud, such as at the aforementioned central hub.

Figure 5:
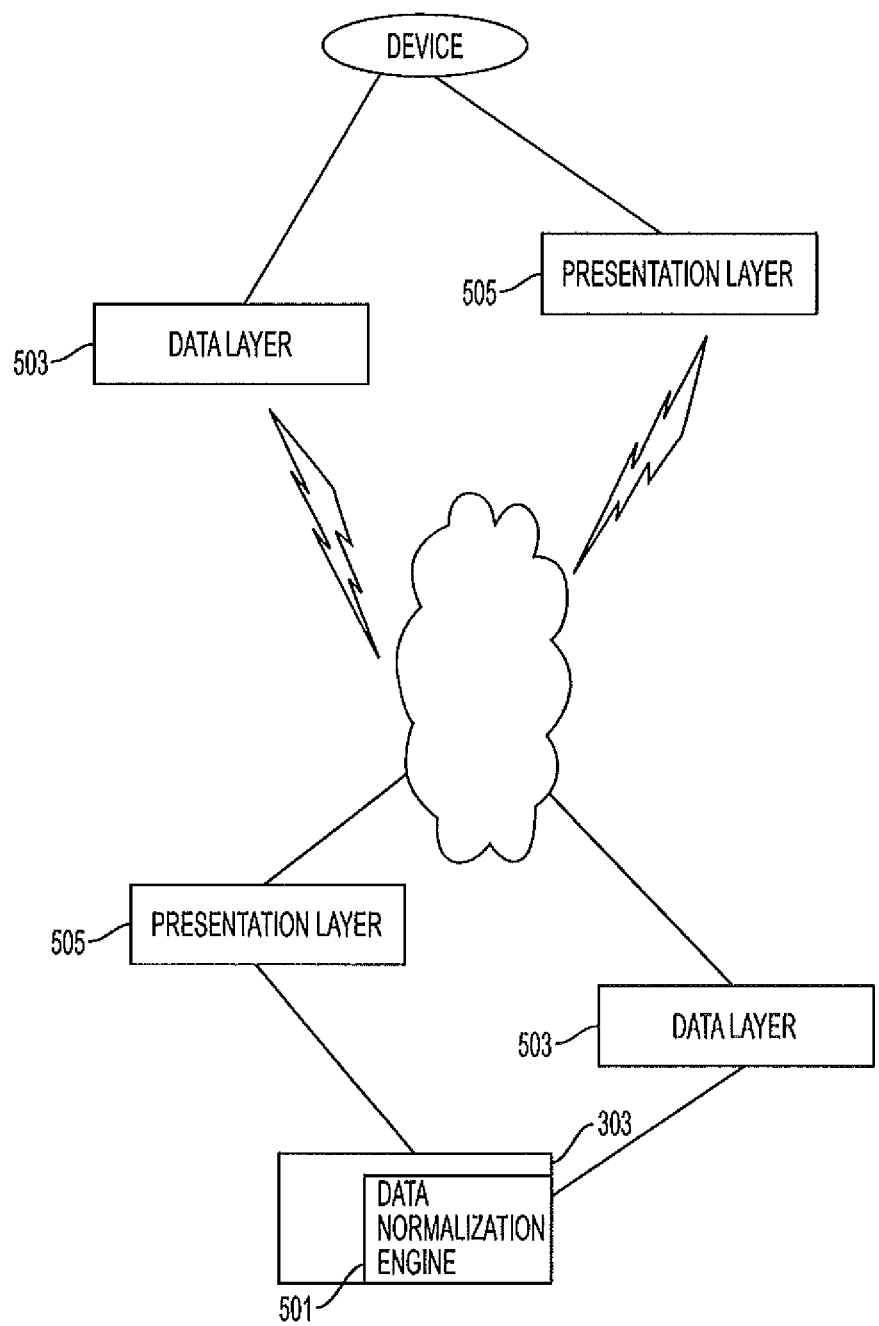
FIG. 5 illustrates a normalization engine according to embodiments of the present invention.

FIG. 5 illustrates a data normalization engine 501, resident at central hub 303, that provides data layer services 503. Further illustrated in FIG. 5 is a presentation layer 505 that may assess a presentation in the local surgical environment, and that may further select a presentation for the remote app based on data, and/or that provides to the user data, indicated at data layer 503.

Simply put, local surgical environment data may be read by the data normalization engine 501 as to data layer services, such as machine languages and spoken languages in the local environment; the data may be normalized at the central hub 303 into a particular language for data employed by the central hub; and the data may be translated outbound in the data layer 503 into a different machine language and/or a different spoken language for presentation as directed by the presentation layer 505 to a remote user of the app. This data normalization may be extended to, for example, preferred surgical procedure and technique data, or the like.

Thereby, the presentation of the remote user app may itself be normalized across many operating systems, and as such variable presentations may be provided on a laptop, desktop, a cellular device, a tablet computer, or the like. The presentation device for the remote user may be a matter of preference, such as wherein the remote user may prefer a larger screen in order to be able to better view the displayed procedure. Further, this data normalization may allow for use of the present invention irrespective of wired or wireless techniques employed as to the surgical devices in a local surgical environment. That is, the local environment may employ Bluetooth for wireless communications, infrared for wireless communications, or the like, and, once the data and presentation is locally read and transferred to the central hub, the data normalization that occurs prior to ultimate presentation to the remote user may allow for an agnostic system and method as to factors, such as the wireless reading technology employed, in the local surgical environment.

In a particular exemplary embodiment, the disclosure may be used to remotely control a "signature" surgical system. A universal app may be provided, for example, for use on an iPhone that allows for remote control of the signature system. The iPhone app may allow for navigation of the controls of the signature system by displaying on the remote user's interface a display screen similar to or the same as that of the signature system in the local surgical environment. Thereby, for example, when a remote user wishes to change from phaco mode to IA mode, the remote app may display the pertinent information pertaining to the mode switch, just as is displayed in the local surgical environment. Thus, the remote user interface would be context sensitive to what the surgeon is attempting to accomplish. The remote app may thus display not only the appropriate setting variables, but additionally may provide dynamically changing available commands or responses, as might be provided locally in a signature system. Further, the signature system may pair locally to a wireless hub, such as using Bluetooth, and the wireless hub may ultimately provide connection to the central hub in the cloud, and from the cloud may be provided the connection to the remote user interface.

Moreover, the collection, or logging, of data residing in the data layer simplifies the data export process, such as for peer review cases or remote user presentations. More specifically, a surgeon may readily have access to all pertinent data on a smart device, without the need for portable memory, such as a USB flash drive. Thus, if the surgeon were giving a presentation, for example, the surgeon would simply be able to access data for a particular surgery, or across many surgeries, by accessing the central hub of the disclosure.

Figure 6:
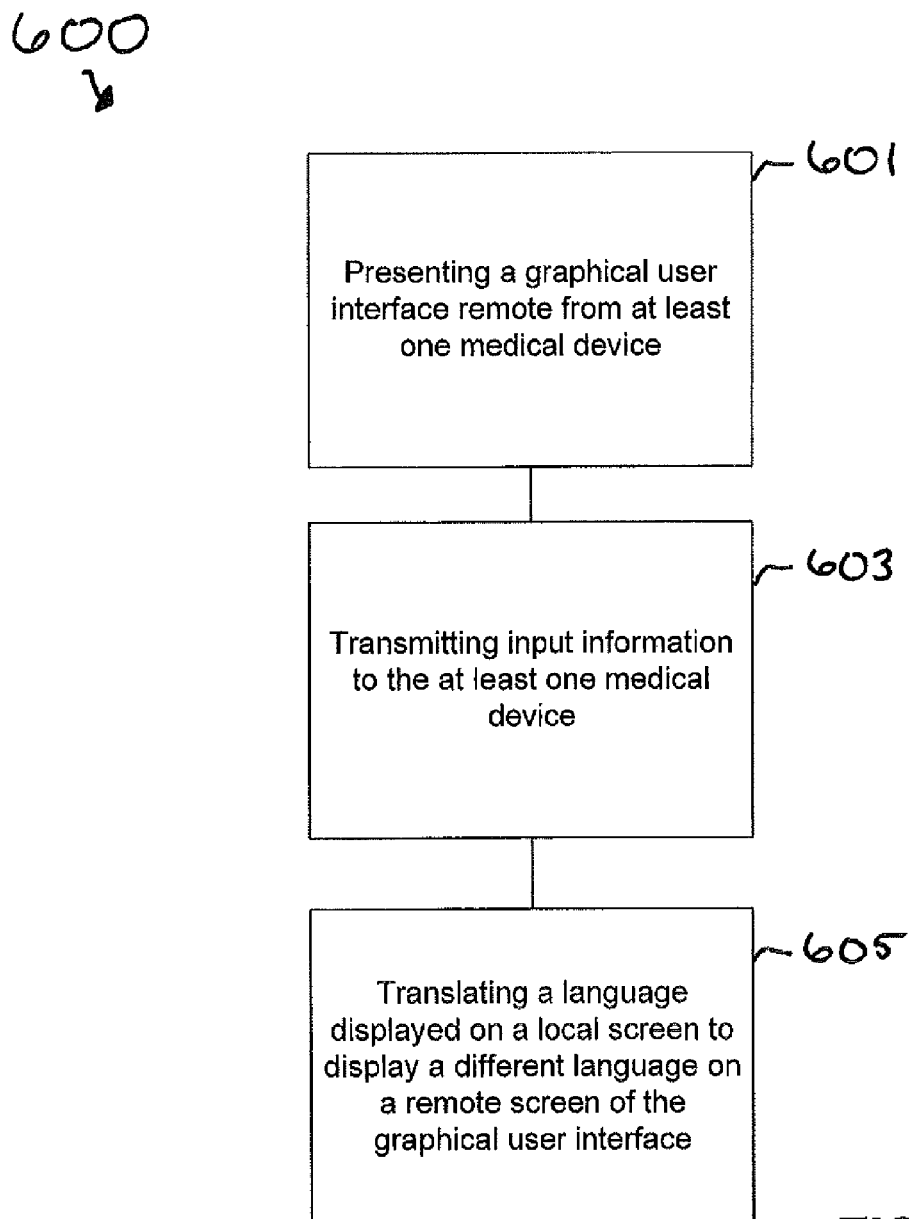
FIG. 6 illustrates a method of remotely controlling a medical device according to embodiments of the present invention.

In accordance with one or more embodiments described herein, and with reference to FIG. 6, there is shown a methodology 600 according to embodiments of the present invention. It is noted that numbers associated with the blocks of FIG. 6 do not imply a particular order in which the corresponding steps are to be performed according to the method 600. In FIG. 6, step 601 includes presenting a graphical user interface remote from at least one medical device. Step 603 includes transmitting input information to the remote user interface to the local at least one medical device, wherein the at least one medical device operates responsively to the received input information. Optionally, at Step 605, the method includes translating a language displayed on a local screen associated with the at least one medical device to display a different language on the remote screen of the graphical user interface, and/or translating available or received commands from a first machine language used in the local surgical environment to a second machine language used on the remote user interface.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein but is to be accorded the widest scope consistent with the principles and novel features disclosed herein.

What is claimed is:

1. A system for remotely controlling at least one medical device over a network, the system comprising:
a non-transitory computer readable medium having encoded thereon computer executable instructions for:
a graphical user interface capable of providing remote user input to the at least one medical device, wherein the graphical user interface is at least substantially a true screen representation of an interface of the at least one medical device, and
logging medical device parameters and settings from the at least one medical device across one or more surgical procedures, wherein the medical device parameters and settings related to a particular surgeon, patient, patient type, surgeon type, equipment type, surgical procedure type, supply inventory, parameter, or device setting type;
providing a recommendation to the remote user based on the logged medical device parameters and settings;
at least one network port communicably coupled to the at least one medical device, capable of remotely receiving the input information, wherein a driver locally associated with the at least one medical device is configured to control the at least one medical device responsively to the input information; and
a normalizing engine configured to:
read local environmental data associated with a local environment of the at least one medical device, the local environmental data including at least one of at least one machine language or at least one spoken language corresponding to the local environment of the at least one medical device, and
translate the local environmental data into at least one of a different machine language or a different spoken language for presentation of the graphical user interface,
wherein the at least one medical device is in a surgical environment,
wherein the graphical user interface comprises a displayed screen displaying controls substantially similar to the interface of the at least one medical device,
wherein the displayed screen and the interface of the at least one medical device display substantially identical content, and
wherein the displayed screen is capable of displaying the content associated with at least two of the at least one medical device simultaneously.

2. The system of claim 1, wherein the normalizing engine is further configured to dynamically select between a plurality of different graphic user interfaces that each correspond to the true screen representation of the interface of the at least one medical device for presentation of the graphic user interface.

3. The system of claim 1, wherein the logged medical device parameters and settings is stored in a database communicatively and remotely associated with the at least one medical device.

4. The system of claim 1, wherein the logged medical device parameters and settings comprises log files associated with the at least one medical device.

5. The system of claim 1, wherein the graphical user interface is provided on a mobile device.

6. A non-transitory computer readable storage medium having encoded thereon computer executable instructions for a computer-implemented method of remotely controlling at least one electronic device in an optical surgical environment, comprising:
presenting a graphical user interface that provides user interactive controls substantially similar to and remote from those provided by the at least one electronic device;
transmitting information input to the graphical user interface to the at least one electronic device, wherein the at least one electronic device operates responsively to the received input information;
logging medical device parameters and settings from the at least one medical device across one or more surgical procedures, wherein the usage information is related to a particular surgeon, patient, patient type, surgeon type, equipment type, surgical procedure type, supply inventory, parameter, or device setting type;
providing a recommendation to the remote user based on the logged medical device parameters and settings;
reading local environmental data associated with a local environment of the at least one electronic device, the local environmental data including at least one of at least one machine language or at least one spoken language corresponding to the local environment of the at least one electronic device; and
translating the local environmental data into at least one of a different machine language or a different spoken language for presentation of the graphical user interface, wherein the at least one electronic device is in a surgical environment, wherein the graphical user interface comprises a remote screen displaying spoken language that is the same as that displayed on the electronic device, wherein the remote screen and the electronic device display the same content, and wherein the graphical user interface is capable of displaying substantially similar content to at least two of the at least one electronic device simultaneously and alternately.

7. The medium of claim 6, wherein the medical device parameters and settings is stored in a database communicatively and remotely associated with the at least one medical device.

8. The medium of claim 6, wherein the medical device parameters and settings comprises log files.

9. The medium of claim 6, wherein the graphical user interface is provided on a mobile device.

10. A method for remotely controlling at least one optical surgical device over a network, comprising:

presenting a substantially true screen graphical user interface to a user remote from the at least one optical surgical device; and transmitting information input to the substantially true screen graphical user interface to the at least one optical surgical device to operate the optical surgical device responsively to the received input information;

reading local environmental data associated with a local environment of the at least one electronic device, the local environmental data including at least one of at least one machine language or at least one spoken language corresponding to the local environment of the at least one electronic device;

translating the local environmental data into at least one of a different machine language or a different spoken language for presentation of the graphical user interface;

logging medical device parameters and settings from the at least one optical surgical device across one or more surgical procedures, wherein the usage information is related to a particular surgeon, patient, patient type, surgeon type, equipment type, surgical procedure type, supply inventory, parameter, or device setting type; and providing a recommendation to the remote user based on the logged medical device parameters and settings, wherein the at least one optical surgical device is in a surgical environment, wherein the graphical user interface comprises a remote touch screen, wherein the remote touch screen and the at least one optical surgical device display the same content, and wherein the remote touch screen is capable of displaying the content associated with at least two of the at least one optical surgical device simultaneously.

11. The method of claim 10, wherein the same content is in two different spoken languages.

12. The method of claim 11, further comprising translating a first of the two spoken languages to a second of the spoken languages.

* * * * *